United States Patent [19]

Hummel

[11] 4,280,232
[45] Jul. 28, 1981

[54] INTRAOCULAR LENS DEVICE

[76] Inventor: Robert A. Hummel, 4200 W. Memorial Rd., Suite #308, Oklahoma City, Okla. 73120

[21] Appl. No.: 144,683

[22] Filed: Apr. 28, 1980

[51] Int. Cl.³ .............................................. A61F 1/16
[52] U.S. Cl. ......................................................... 3/13
[58] Field of Search ................................................ 3/13

[56] References Cited

U.S. PATENT DOCUMENTS 3,906,551  9/1975  Otter ......................................... 3/13

*Primary Examiner*—Clifford D. Crowder
*Attorney, Agent, or Firm*—Robert M. Hessin

[57] ABSTRACT

An artificial intraocular lens device which utilizes a distendable, resilient superior loop and affixure to form a lobular positioning structure for implantation. The lens includes a superior haptic rim and large superior loop that may be secured to the haptic rim to provide spring-like lobes. In addition, various configurations of inferior loop and/or inferior haptics may be utilized in combination to provide a pseudophakia for implantation in the anterior chamber, transiridial position, or posterior chamber.

17 Claims, 9 Drawing Figures

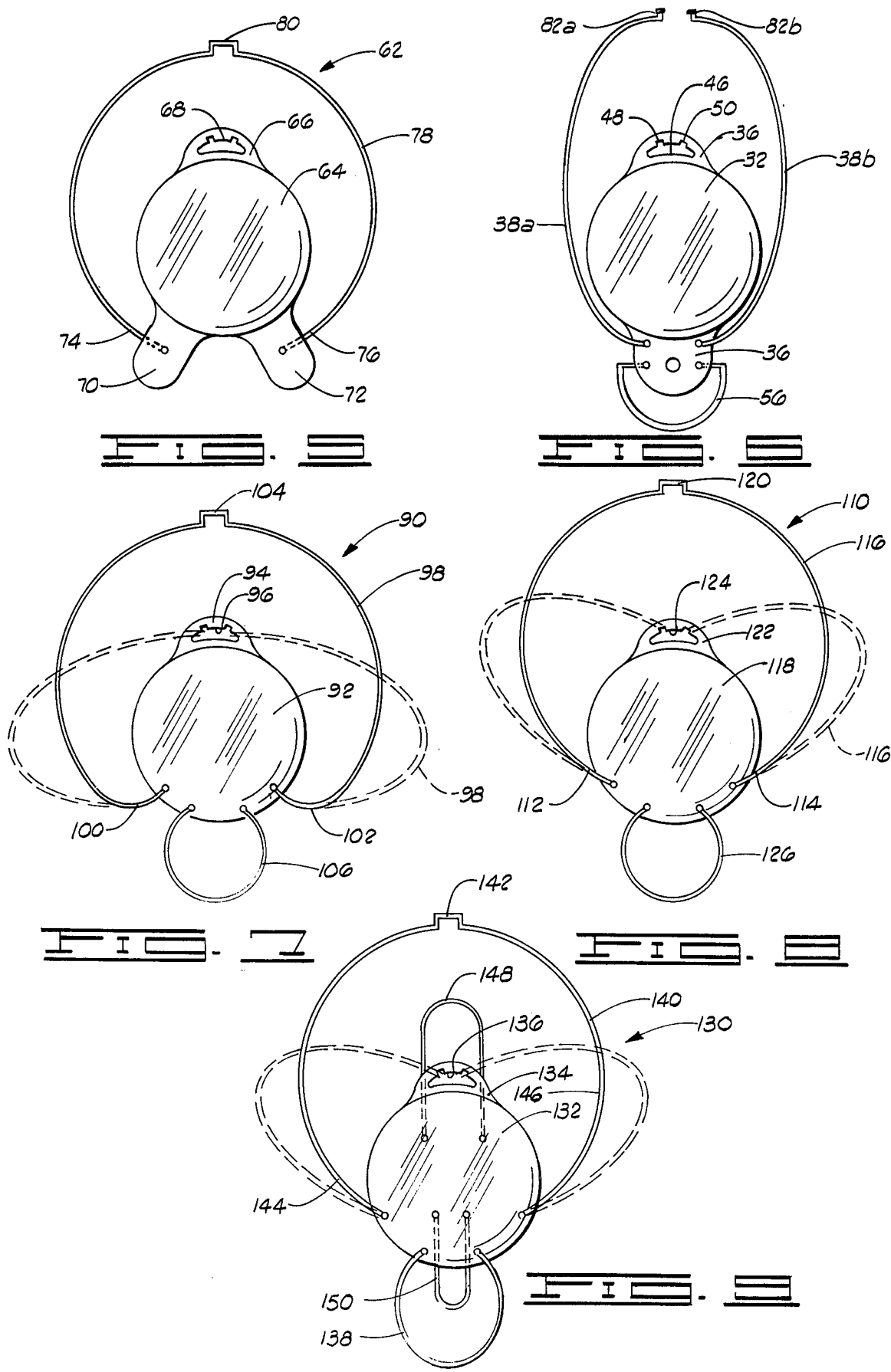

INTRAOCULAR LENS DEVICE

BACKGROUND OF THE INVENTION

1. Field of the Invention

The invention relates generally to pseudophakia and, more particularly, but not by way of limitation, it relates to improved artificial intraocular lenses and their attachment or retention appendages.

2. Description of the Prior Art

The prior art includes numerous types of artificial lens device for intraocular dispostion wherein wire loops or other resilient plastic fibers are utilized as attachment appendages. Such artificial lens devices have been implanted in the eye in either the anterior or posterior chambers with affixation by suture to the iris of the eyeball. More recently, a group of devices have been developed which employ transiridial affixation within the eye; that is, appendage or loop means are provided for support on both the anterior and posterior sides of the iris in support of the artificial lens. U.S. Pat. No. 3,906,551 discloses an artificial lens that is designed to include wire loop and/or snap-hook means for transiridial affixation of the intraocular lens in the eye.

U.S. Pat. No. 3,975,779 discloses an artificial lens for insertion in the anterior chamber which includes a plurality of affixation appendages that provide transiridial affixation. This lens includes flexible spring-like members which grip within the pupillary hollow and follow the dilation and contraction movements while also providing centration of the artificial lens. U.S. Pat. No. 4,014,049 discloses a similar form of transiridially affixed artificial lens which is suitable for either anterior or posterior chamber installation and, here again, flexible spring-like members are formed for gripping engagement within the pupillary opening.

SUMMARY OF THE INVENTION

The present invention relates to an improvement in artificial intraocular lenses wherein affixation appendages are adapted for lens implantation in the anterior or posterior chamber of the eye or, more particularly, in the posterior chamber and in enclosure within the capsular bag after extracapsular lens removal, in the condition of aphakia. The lens device includes the lens portion, anterior and posterior surfaces which are optically finished to the desired optical correction, and support appendages are then formed thereon. Particularly, there is a superior haptic rim, including locking fenestration, and a superior loop formed of resilient spring-like material and having opposite ends secured to a lower edge of the lens while the loop extends around the lens in significantly larger dimension with capability of being moved into interlocking engagement with the fenestration thereby to provide extended lateral lobes when finally seated in operative disposition adjacent the iris of the aphakic eye. To further aid in securing the lens device within the aphakic eye, additional inferior haptic rim configurations and/or inferior loops are utilized, the particular form and shape being a function of intended usage of the lens device, i.e. whether it shall be implanted in the anterior chamber, posterior chamber, intracapsularly within the posterior chamber, or transiridial position.

Therefore, it is an object of the present invention to provide an artificial intraocular lens device which may be more securely positioned within an aphakic eye while allowing necessary freedom of the iris and adjacent tissues.

It is also an object of the present invention to provide an artifical intraocular lens that may be permanently implanted with less likelihood of excessive loss of vitreous body fluid or other permanent damage to the eyeball.

It is still further an object of the present invention to provide an artificial intraocular lens which is more easily implanted within an aphakic eye through a smaller incision, and yet more secure in positioning, during existence under normal stresses, owing to wider supporting loop (lobes) effected by interlocking the superior loop with the haptic fenestration.

Finally, it is an object of this invention to provide an intracapsular intraocular lens that is more stable in disposition and requires fewer securing procedures to finalize implantation.

Other objects and advantages of the invention will be evident from the following detailed description when read in conjunction with the accompanying drawings which illustrate the invention.

BRIEF DESCRIPTION OF THE DRAWINGS

FIG. 5 is a plan view of an alternative form of lens device;

FIG. 6 is an alternative view of still another form of lens device;

FIG. 7 is a plan view of a lens device that is specifically adapted for posterior chamber implantation;

FIG. 8 is a plan view of a lens device that is specifically adapted for anterior chamber implantation; and FIG. 9 is a plan view of a lens device that is specifically adapted for transiridial implantation.

DETAILED DESCRIPTION OF THE PREFERRED EMBODIMENT

Figure 1:
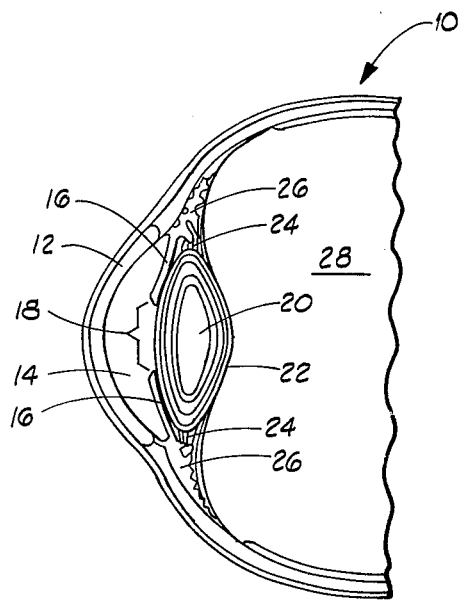
FIG. 1 is a partial section in idealized form of a human eyeball.

FIG. 1 depicts a human form eyeball 10 and the basic anatomical parts thereof. The eyeball 10 consists of the outer cornea 12 that encapsulates the anterior chamber 14 and iris 16 which defines the pupillary aperture 18. Immediately posterior to iris 16 is the lens 20 as maintained within the lens capsule or capsular bag 22 in complete surround. The lens 20 is maintained in position by means of the lens capsule 22, and epithelial cell structure, which is circumferentially suspended by means of zonular fibers 24 as connected to the ciliary processes and ciliary muscle, shown generally at 26. Immediately behind the lens 20 and capsular bag 22 lies the vitreous cavity 28 which contains the vitreous body.

At present, implantations of pseudophakia or artificial intraocular lenses are carried out by affixing an artificial lens anteriorly or in the anterior chamber just in front of the iris 16 or posteriorly just behind the iris 16. In either case, it is the aim to secure the refracting lens portion in reliable affixure within the pupillary aperture 18 so that optical focusing is effected to the retina (not shown) at the rear of the eyeball.

Figure 4:
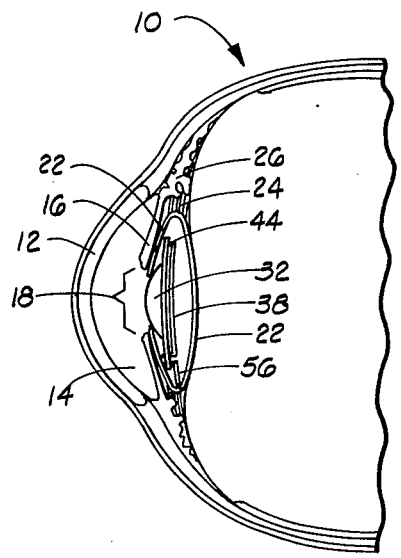
FIG. 4 is a vertical section of the eyeball in idealized form with the intracapsular lens device of FIGS. 2 and 3 shown implanted.

The present invention is concerned with the intraocular creation of wider supporting appendages of an intraocular lens that has been introduced into the eye through a small incision. This is accomplished by collapsing a larger superior loop and interlocking it with a haptic fenestration to form wider lateral lobes (loops) than could be inserted through a specially small incision. Thus, as in the case of a cataractous lens 20, an opening is made in the anterior surface of the capsular bag 22, generally in the area adjacent the pupillary aperture 18. Thereafter, the damaged lens tissue 20 is removed by means of a vacuum tool or the like and the intracapsular lens is positioned in secure implantation within the capsular bag 22, as shown in FIG. 4 and to be further described.

Figure 2:
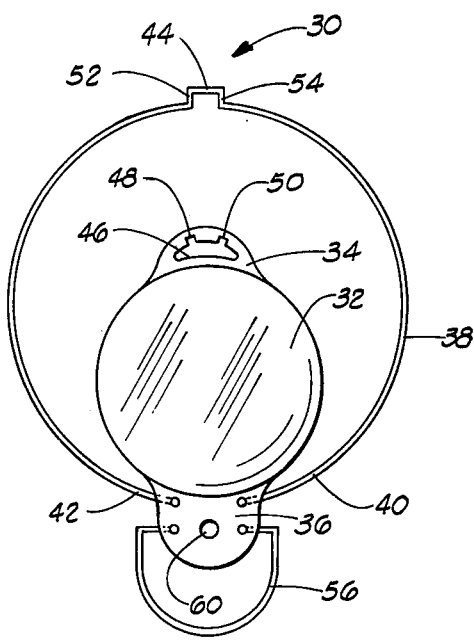
FIG. 2 is a plan view of a lens device constructed in accordance with the present invention.

Referring to FIG. 2, an intraocular lens 30 is particularly adapted for insertion and affixure within the capsular bag 22. A lens element 32 is unitarily formed to include a planar form superior haptic rim 34 and an oppositely disposed inferior haptic rim 36. The lens portion 32 is of course optically formed to provide the prescribed refractive indices to the anterior and posterior surfaces, and the lens 32 is optically finished to provide requisite transparency. A superior loop 38 is secured with first and second ends 40 and 42 secured in the inferior haptic rim 36 to extend around lens 32 in generally the same plane and with nearly two times the diameter. The diameter of superior loop 38 is critical as to its inserted width when in the FIG. 3 or locked position. Thus, superior loop 38 includes a stirrup 44 formed at its midportion and adapted to be interlocked within the opening or fenestration 46 formed in superior haptic rim 34.

Figure 3:
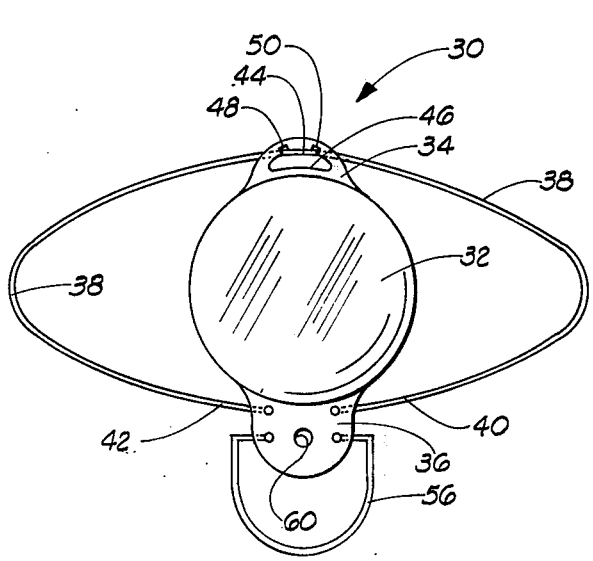
FIG. 3 is a plan view of the lens device of FIG. 2 when the locking appendage is in the implantation attitude.

As also shown in FIG. 3, the fenestration 46, formed as an arcuate segment, includes a pair of spaced, radially oriented ear slots 48 and 50 which are utilized to secure the stirrup 44 by receiving respective stirrup sides 52 and 54 in interlocked engagement. In the interlocked position, the superior loop 38 should have a width that adapts for firm lateral seating within the capsular bag 22. Thus, the length of each spring-like lobe, i.e. the opposite lobes of superior loop 38 and inferior loop 56, should each extend on the order of 6 to 6.25 millimeters from the center of lens portion 32.

The lens 32 and haptics may be formed from any of the presently used optical materials which are inert within their operational environment. For example, the lens material may be a polymethyl methacrylate which is commercially available for optical usage under the trademark "PERSPEX C-Q". The superior and inferior loops 38 and 56 are resilient plastic fiber materials that have a spring-like property, and loops 38 and 56 may be formed from such as polypropylene fiber that is commercially available under the trademark "PROLENE" as available from Ethicon Inc. The spring-like loops may be formed from various other biologically inert materials, both metal and plastic, all of which are well-known in the related art.

The loops 38 and 56 are secured within the haptic rim 36 by heat joining the free ends within preformed holes and permanent bends or configurations of the loops are heat formed in well-known manner. U.S. Pat. No. 3,996,626 illustrates one form of prior art method for securing the biologically inert polymeric materials to the lens structure.

FIG. 4 shows the lens 30 in intracapsular disposition. Thus, after formation of an opening in the anterior, central portion of capsular bag 22, the lens 30 is inserted bottom first with inferior loop 56 seeking the bottom extremity of capsular bag 22. Thereafter, the stirrup 44 portion of superior loop 38 is collapsed toward fenestration 46 while inserting the lateral lobe portions of loop 38 within capsular bag 22 whereupon stirrup 44 is affixed within fenestration 46 and interlock on ear slots 48 and 50. The side lobes of superior loop 38 then seek firm seating in the sides of capsular bag 22 while inferior loop 56 maintains the lens 32 in proper positioning behind the pupillary aperture 18.

Many variations of intraocular lens utilizing an interlocking superior loop become possible, and a number of alternative structures are illustrated in FIGS. 5-9. Referring to FIG. 5, an intracapsular type lens, an intraocular lens 62 consists of a lens 64 extending a superior haptic rim 66 having arcuate fenestration 68. A pair of laterally offset haptic rims 70 and 72 then extend to receive first and second ends 74 and 76 of a superior loop 78. The superior loop 78 includes a heat-formed stirrup 80 at the mid-portion, and stirrup 80 is formed for interlocking engagement within fenestration 68 and the associated ear slots when in intracapsular position.

The lens 62 is similarly inserted through the front opening of a capsular bag 22 with spaced inferior haptics 70 and 72 seeking the downward extremity of capsular bag 22. Thereafter, the superior loop 78 is manipulated into the capsular bag opening and collapsed with interlocking of stirrup 80 within fenestration 68 to extend the lateral lobes into instracapsule seating.

FIG. 6 is an intracapsular lens that is identical to the intraocular lens 30 (FIG. 2) with the exception that the superior loop 38 is divided. Thus, the superior loop is formed as two opposite sides 38a and 38b each formed with a nib 82a and 82b on the respective ends. Thus, this intraocular lens finds utilization in particular applications wherein the pupillary aperture may be smaller than usual and the use of two free-end loops 38a and 38b facilitates insertion of the lens within the capsular bag. Thereafter, the individual nibs 82a and 82b can be interlocked into the respective ear slots 48 and 50 of fenestration 46.

FIG. 7 illustrates an intraocular lens 90 which is used for posterior chamber implantation. That is, lens 90 is implanted in the posterior chamber and the capsular bag 22. The intraocular lens 90 consists of a lens portion 92 which extends a superior haptic 94 including the characteristic arc segment fenestration 96. A superior loop 98 having first and second ends 100 and 102 and midportion stirrup formation 104 is secured adjacent the lower periphery of lens portion 92. Here again, the loop fibers are heat-secured about midway in opposite lower quadrants of lens portion 92, such affixure being near the periphery of the lens so that the central part of lens portion 92 is free for optical light transmission. The first and second ends 100 and 102 are each secured to lens portion 92 so that they extend generally radially from lens portion 92 thereby to provide a generally downward bias to the superior loop 98. Thus, when stirrup 104 is affixed within fenestration 96, as shown by the dash-line illustration, the outward or lateral lobes of superior loop 98 are drawn down to fully lateral extension, i.e. the opposite side lobes of interlocked superior loop 98 are approximately even with the optical axis of lens portion 92.

An inferior loop 106 is also heat-secured to the lower perimeter of lens portion 92, and within the heat affixture points of superior loop first ends 100 and 102, so that lower side lens support is offered for implantation.

Thus, the intraocular lens 90 can be positioned through the pupillary aperture 18 and behind iris 16 (see FIG. 1) with inferior loop 106 seeking a position within the capsular bag 22, and superior loop 104 can be affixed within its fenestration 96 to extend the lateral side lobes of superior loop 98 outward for secure positioning behind the lateral extremities of iris 16. The lobe or loop extensions are equidistant from the lens axis and such three point support serves to maintain intraocular lens 90 with the optical axis of lens portion 92 in alignment within pupillary aperture 18.

Referring to FIG. 8, a similar form of intraocular lens 110 is utilized for anterior chamber implantation. The primary difference in structure between intraocular lens 110 and intraocular lens 90 is the angular placement of first and second ends 112 and 114 of superior loop 116 as they extend from secure affixure to the lower peripheral edges of lens portion 118. The first and second superior loop ends 112 and 114 are heat-secured at approximately the midpoint of opposite lower quadrants of lens portion 118 but they are secured in affixure in such manner that they extend upward and at an angle of approximately 30° from tangency to the periphery of lens portion 118. This positioning places an upward bias on the superior loop 116 so that when its midportion stirrup 120 is affixed within the superior haptic rim 122 and fenestration 124, the side lobes of superior loop 116 (as shown in dash-lines) have a distinctly upward bias which places the outer extremity of the side lobes oppositely adjacent to the superior edge of lens portion 118. The intraocular lens 110 includes an inferior loop 126 which is again secured to the lower edge of lens portion 118 and beneath the point of affixure of superior loop first ends 112 and 114 to provide a spring-like lower support.

In implantation, the intraocular lens 110 need only be positioned in the anterior chamber 14 and in front of iris 16 (see FIG. 1) with the optical axis of lens portion 118 aligned with pupillary aperture 18. The inferior loop 126 will seek a positioning within the angle of anterior chamber 14, immediately in front of iris 16, and the superior loop 116 can then be secured with stirrup 120 in fenestration 124 to extend opposite side lobes of superior loop 116 outward into the angle of anterior chamber 14 and immediately in front of iris 16, but with appropriate clearance of the iris 16.

Finally, the embodiment of FIG. 9 illustrates an intraocular lens which employs the superior loop and is intended for transiridial affixure, i.e. lens loops secure both posterior and anterior to iris 16 (see FIG. 1) and the iris 16 tends to maintain the lens in its proper optical positioning. Thus, an optical lens portion 132 includes superior haptic 134 and fenestration 136 as well as an inferior loop 138 affixed generally centrally to the lower peripheral edge of lens portion 134. A superior loop 140 includes the formation of a stirrup 142 and the first and second ends 144 and 146 are heat-secured at the outer, upper part of the opposite lower quadrants of lens 132 at an angle of approximately 30° from tangency thereby to provide an upward bias to the opposite side lobes of superior loop 140 when the stirrup 142 is affixed in fenestration 136. This configuration then gives a triangle of support anteriorly relative to the center or optical axis of lens 132 when in the affixed position, i.e. similar to the FIG. 8 structure. A second superior loop 148 is affixed to extend from the posterior side of lens 132 and serves to provide a retaining structure behind iris 16 (see FIG. 1). Also, a second inferior loop 150 is heat-secured to extend from the posterior side of lens 132 downwardly for position behind the lower portion of iris 16. Thus, when lens 132 is placed with stirrup 142 secured in fenestration 136, the upper and lower posterior loops 148 and 150 are retained behind iris 16 while the opposite side lobes of superior loop 140 and the inferior loop 138 are securely positioned in the anterior chamber 14 immediately in front of iris 16. The pupillary border of the iris forming the pupillary aperture tends to constrict about the points of lens affixure of posterior superior loop 148 and posterior inferior loop 150 thereby to maintain the optical axis of lens 132 in alignment over pupillary aperture 18.

The foregoing discloses a novel form of intraocular lens which may be implanted with firm positioning and reliable function without the need for certain suture and clamping practices necessary in maintaining the optical element in operative alignment. The lens device, in one of its forms or another, may find usage in any of anterior, posterior, transiridial or intracapsular implantation, and the device is capable of implantation through a small surgical incision and yet more stable owing to wider support loops (lobes) effected by interlocking the stirrup of the superior loop into the fenestration in the haptic. While the superior loop and haptic affixure are primary facets of the lens device, it should be understood that various combinations of the inferior spring members, angular lobing and the like are possible and entirely within the scope of the present invention.

Thus, changes may be made in combination and arrangement of the elements as heretofore set forth in the specification and shown in the drawings; it being understood that changes so made reside within the spirit and scope of the invention as defined in the following claims.

What is claimed is:

1. An artificial intraocular lens device, comprising:
   a lens having anterior and posterior surfaces formed to provide prescribed optical focal properties;
   a superior haptic rim of planar form extending from an upper edge of said lens and including a fenestration therethrough;
   a superior loop of resilient material having first and second ends secured adjacent the lower edge of the lens and extending circularly around said lens while having greater width than said lens; and
   stirrup means formed in the mid-portion of said superior loop which may be forced into affixation within said fenestration thereby to laterally extend the opposite side lobes of said superior loop.

2. A lens device as set forth in claim 1 which further comprises:
   an inferior haptic rim of planar form extending from the lower edge of said lens.

3. A lens device as set forth in claim 2 which further comprises:
   inferior loop means formed of resilient material and having first and second ends secured in said inferior haptic rim to extend generally semi-circularly around the lower edge of said inferior haptic rim.

4. A lens device as set forth in claim 3 wherein:
   said superior loop opposite side lobes and said inferior loop means extend equi-distant from the optical axis of said lens.

5. A lens device as set forth in claim 1 wherein:
   said fenestration is formed generally as an arc segment with first and second spaced ear slots formed in radial alignment on the arcuate edge.

6. A lens device as set forth in claim 5 wherein said stirrup means comprises:
a rectangular permanent set placed in said superior loop, said rectangle dimension matching said fenestration ear slot spacing to enable interlocking engagement.

7. A lens device as set forth in claim 6 which further comprises:
an inferior haptic rim of planar form extending from the lower edge of said lens.

8. A lens device as set forth in claim 7 which further comprises:
inferior loop means formed of resilient material and having first and second ends secured in said inferior haptic rim to extend generally semicircularly around the lower edge of said inferior haptic rim.

9. A lens device as set forth in claim 1 wherein:
said superior loop is formed of two segments having said first and second ends and first and second stirrup ends; and
said stirrup means are formed on each of the first and second stirrup ends for interlocking engagement in said fenestration.

10. A lens device as set forth in claim 1 which further comprises:
first and second inferior haptic rims, each of planar form and extending from the lower edge of said lens in spaced relationship.

11. A lens device as set forth in claim 10 wherein:
said superior loop first and second ends are secured in respective first and second inferior haptic rims.

12. A lens device as set forth in claim 1 wherein:
said superior loop first and second ends are secured to respective peripheral mid-points of opposite lower quadrants of the lens to extend radially therefrom and impose a downward bias on said superior loop.

13. A lens device as set forth in claim 12 which further comprises:
an inferior loop means formed of resilient material and having first and second ends secured to the lower edge of said lens.

14. A lens device as set forth in claim 13 wherein:
said superior loop opposite side lobes and said inferior loop means extend equi-distant from the optical axis of said lens.

15. A lens device as set forth in claim 1 wherein:
said superior loop first and second ends are secured to respective peripheral mid-points of opposite lower quadrants of the lens to extend therefrom upwardly at thirty degrees to tangency thereby to impose an upward bias on said superior loop.

16. A lens device as set forth in claim 15 which further comprises:
an inferior loop means formed of resilient material and having first and second ends secured to the lower edge of said lens.

17. A lens device as set forth in claim 16 which further comprises:
second superior loop means secured to said lens and extending generally parallel to said superior loop for upper posterior iridial disposition; and
second inferior loop means secured to said lens and extending generally parallel to said inferior loop means for lower posterior iridial disposition.

* * * * *